United States Patent [19]

Moore

[11] Patent Number: Plant 5,376

[45] Date of Patent: Dec. 25, 1984

[54] ROSE PLANT

[75] Inventor: Ralph S. Moore, Visalia, Calif.

[73] Assignee: Sequoia Nursery, Visalia, Calif.

[21] Appl. No.: 461,985

[22] Filed: Mar. 25, 1983

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by small yellow and orange colored buds and flowers.

1 Drawing Figure

1

The present invention relates to a new and distinct variety of hardy, dwarf, bush type rose plant of the miniature class; the variety being primarily characterized—as to novelty—by the yellow and orange coloring of its flowers which generally open quite flat and hold colors extremely well.

The variety is further characterized by:

An abundance of bloom, with flowers usually borne several to the stem in small clusters/sometimes singly.

Little or no fragrance.

A plant which is moderately vigorous, of rounded, upright shape with small semi-glossy foliage with pointed leaflets; the buds and flowers being similar in form to Lemon Delight (miniature—U.S. Plant Pat. No. 4,447) but smaller and with more petals.

The plant, which has a normal height of 10–12 inches (taller in greenhouse) can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Rumba (U.S. Plant Pat. No. 1,919, expired—floribunda) as the seed parent and Lemon Delight (U.S. Plant Pat. No. 4,447—miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification; MORlem—(-Commercial synonym: SUN GOLD).

Flowers borne: several together (3 to 5) on slender wirey stems (sometimes singly).

Quantity of bloom: Abundant both outside and in greenhouse.

2

Bud:

*Peduncle.*—Medium length; slender but sturdy; erect; medium green, sometimes tinted bronze (outdoors); with numerous short hairs.

*Before calyx breaks.*—Size — small. Form. long, ovoid to pointed, with several small foliaceous appendages and numerous short hairs on surface of bud; with foliaceous parts extending beyond the tip of the bud equal to one-half or more of its length.

Color: Medium green, occasionally tinted with bronze (outdoors).

*As calyx breaks.*—Color — greenish to yellow. Opening: opens well in all weather.

Bloom:

*Size when fully open.*—Small, averaging about 25 mm (1").

*Petalage.*—Double — averaging about 18 petals, arranged regularly plus an occasional petaloid.

*Form.*—Cupped at first and remaining cupped to flat. Open flowers usually have stamens.

Petals: Fairly thick; satiny on inside and on outside surface.

*Shape.*—Outside petals, broad lanceolate with very short acute tip; intermediate — broad lanceolate with very short acute tip; inside — lanceolate with acute tip.

Inside surface: Bright yellow, near Maize Yellow 607 (or similar) on basal $\frac{1}{3}$ of petal, changing or blending into an orange red (or brickish red) near Nasturtium Red 14/2. This red color is underlaid and modified with yellow and may vary with the season and intensity of the sunlight.

Intermediate petal: Outside surface — similar to outside petal. Inside surface similar to outside petal.

Inner petal: Outside surface — similar to intermediate petal; inside surface — similar to intermediate petal. General color effect; newly opened flowers — color — bright orange with yellow "eye". Three days open — color-similar to fresh open flowers, but less bright. Behavior — opens well in all weather. Spent petals or flowers drop off. Flower longevity (July–August 1982) — plant in pot 6–10 days or longer. Cut flowers at living room temperature — 5–7 days or longer.

Reproductive organs:

*Stamens.*—Average number.

*Filaments.*—Varying length.

*Anthers.*—Yellow.

*Pollen.*—Little or none.

*Pistils.*—Average number.

*Styles.*—Varying length; yellow; bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; small; leathery; glossy.

*Leaflets.*—Shape: broad, calceolate; apex acute; base — acute; sometimes rounded.

*Color.*—Medium green; new growth — normal (medium) green (sometimes tinted reddish).

*Rachis.*—Medium strength; upper side may have a few very short hairs; grooved; underside may have several small thorns (or claws) and few to no short prickles.

*Stipules.*—Medium to short length; medium width; medium to short length narrow points which turn out usually at about 45 degrees or less.

Growth:

*Habit.*—Dwarf; bushy; upright; much branched.

*Growth.*—Moderately vigorous; internodes short.

*Canes.*—Medium; slender; sturdy.

*Main stems.*—Color: medium green.

*Thorns.*—Several — of varying size and length — curved to straight; color — grey. Hairs; few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of yellow and orange, being yellow on center portion of flower with outer band of orange to orange red, the bud being pointed in the early opening stage, resembling in form Lemon Delight — miniature — U.S. Plant Pat. No. 4,447, with the full open flower being flat to slightly cupped, with 18 or more petals; and further characterized by a plant of compact, vigorous, well rounded shape, with main stems and shoots of average thorniness, the said plant being easy to propagate from soft wood cuttings, with an abundance of small semi-glossy to matt foliage, the flowers being born singly or several to the stem in clusters.

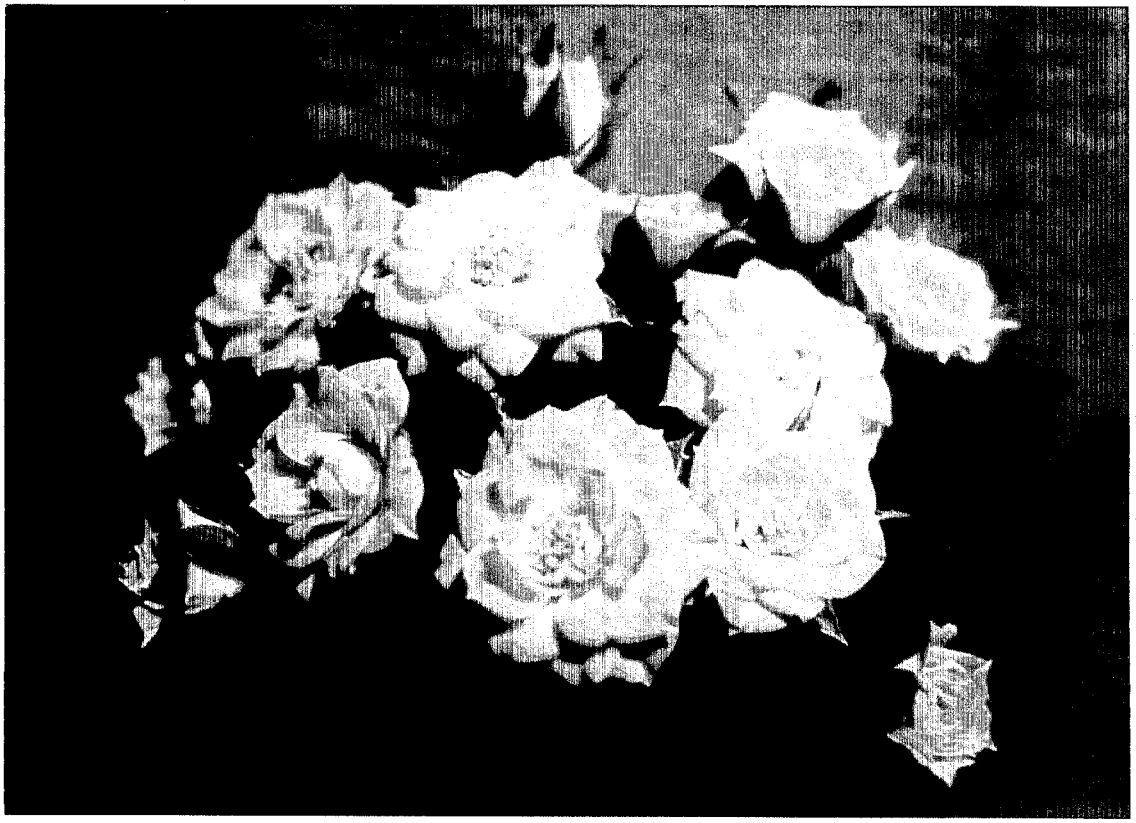

* * * * *